(12) United States Patent
Kulprathipanja et al.

(10) Patent No.: US 6,346,645 B1
(45) Date of Patent: Feb. 12, 2002

(54) ADSORPTIVE REMOVAL OF CARBONYL IMPURITIES FROM OXYGENATED ORGANIC LIQUIDS

(75) Inventors: Santi Kulprathipanja, Inverness; David W. House, Arlington Heights; Peter R. Pujado, Palatine, all of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/551,642

(22) Filed: Apr. 18, 2000

(51) Int. Cl.⁷ ............................................. C07C 51/12
(52) U.S. Cl. ...................... 562/519; 562/519; 562/608
(58) Field of Search ................... 562/519, 608

(56) References Cited

U.S. PATENT DOCUMENTS

| | | | |
|---|---|---|---|
| 3,769,329 A | 10/1973 | Paulik et al. | 260/488 |
| 5,001,259 A | 3/1991 | Smith et al. | 562/519 |
| 5,132,456 A | 7/1992 | King et al. | 562/593 |
| 5,155,265 A | 10/1992 | Scates et al. | 562/608 |
| 5,334,755 A | 8/1994 | Yoneda et al. | 562/519 |
| 5,371,286 A | 12/1994 | Blay et al. | 562/519 |
| 5,625,095 A | 4/1997 | Miura et al. | 562/519 |

FOREIGN PATENT DOCUMENTS

| | | | |
|---|---|---|---|
| CA | 2052435 | 4/1993 | |
| DE | 3512352 | 10/1985 | |
| EP | 0 487 284 A2 | 11/1991 | C07C/53/08 |
| EP | 0487284 | * 5/1992 | |
| JP | 2737290 | 4/1998 | |
| SU | 695996 A | 11/1979 | |

* cited by examiner

*Primary Examiner*—Paul J. Killos
*Assistant Examiner*—Farhad Forohar
(74) *Attorney, Agent, or Firm*—John G. Tolomei; John F. Spears, Jr.

(57) ABSTRACT

Carbonyl compounds (e.g. acetone and acetaldehyde) are often present as impurities in oxygenated organic liquids such as acetic acid made by the carbonylation of methanol or in phenol produced by the oxidation of cumene. These impurities can render petrochemical products unsuitable for long-term storage or otherwise adversely affect downstream processing operations. It has now been found that detrimental carbonyl impurities can be easily removed from oxygenated organic liquids by contact with resins having amine functional groups.

20 Claims, No Drawings

ADSORPTIVE REMOVAL OF CARBONYL IMPURITIES FROM OXYGENATED ORGANIC LIQUIDS

FIELD OF THE INVENTION

The present invention relates to a novel method for treating an oxygenated organic liquid stream contaminated with a carbonyl impurity such as acetaldehye or acetone. Contacting the organic liquid with a resin having an amine functional group effectively removes the undesired carbonyl compounds.

BACKGROUND OF THE INVENTION

Adsorptive techniques to remove carbonyl compound impurities have been applied for different reasons to a variety of industrial product streams. For example, Japanese patent 2737290 discloses the use of mineral acid salts of hydrazine-group containing ion exchange resins for the removal of aldehydes from waste water. The adsorptive separation reduces the odor of contaminated water. Canadian patent application 2052435describes the use of a solid nonionic polystyrene adsorbent to remove unsaturated aldehydes, thereby improving beverage (e.g. beer) stability and taste. U.S. Pat. No. 5,132,456 sets forth a process for separating carboxylic acids from aqueous feedstocks by contact with an acid-sorbing phase that can include a weakly to moderately basic anion exchange resin.

The adsorption of carbonyl compounds from hydrocarbon streams, particularly olefinic liquids, has proven beneficial in terms of facilitating downstream processing operations. In German patent 3512352, for example, the adsorptive removal of carbonyl sulfide from a propene stream is carried out to improve its quality as a feedstock for subsequent polymerization in the presence of a Ziegler catalyst. The adsorbent material in this case is an anion exchange resin having an amine function. Soviet Union patent application 695996 discloses several types of resins effective for the removal of carbonyl compounds from isobutylene. The purification of this feed is taught to improve the quality of the butyl rubber end product, resulting from the copolymerization of the purified isobutylene with isoprene.

In addition to carbonyl compound removal from liquid aqueous and hydrocarbon streams, the prior art has also addressed the need to free oxygenated organic liquids of these reactive impurities. Of particular concern is the purification of carboxylic acids, (which are themselves carbonyl compounds) containing trace amounts of carbonyl impurities such as aldehydes and ketones. It is well documented that these impurities invariably contaminate commercial acetic acid products resulting from the catalytic carbonylation of methanol with carbon monoxide, a process that serves as the basis for virtually all new acetic acid capacity. Acetic acid is industrially significant, mainly due to its use in the production of purified terephthalic acid and vinyl acetate monomer.

Methods for manufacturing acetic acid by methanol carbonylation that have proven commercially successful are described in U.S. Pat. No. 3,769,329, and more recently in U.S. Pat. No. 5,001,259. The '259 patent discloses a method for maintaining high catalyst activity and stability in the methanol carbonylation environment by using a specified amount of iodide ions above that which is normally present as methyl iodide or other organic iodide promoter. A distinguishing characteristic of this process, compared to that described in the earlier '329 patent, is the ability to achieve competitive reaction rates and prevent catalyst precipitation at reactor water levels of only 4 wt-% or less. In U.S. Pat. No. 5,344,755, another type of low water process is described, where a supported rhodium (i.e. heterogeneous) catalyst is used in place of the homogeneous catalysts set forth in the former '329 and '259 references.

It is recognized in the art that acetic acid produced by methanol carbonylation, and particularly using the low water processes of the aforementioned '259 and '755 patents, contains a considerable amount of byproduct impurities which can be detected based on their reducing action on permanganate solution. Furthermore, these impurities are not easily separable using the conventional distillation schemes downstream of the carbonylation reactor section designed to purify the product acetic acid from catalyst, methyl iodide promoter, water, and methyl acetate. The presence of such impurities is highly undesirable because they adversely affect the product permanganate time, an important commercial test (STM.170) of the acetic acid quality. Even small amounts of reducing impurities can degrade the stability, usefulness, and overall salability of the acetic acid product. Reducing impurities that have been found to significantly impact permanganate time include, but are not limited to, saturated and unsaturated aldehydes, namely acetaldehyde, butyraldehyde, crotonaldehyde, 2-ethyl crotonaldehyde, 2-methyl 2-pentanal, and 2-ethyl butyraldehyde. Additionally, other undesired carbonyl species such as the ketones acetone and methyl ethyl ketone normally exist to some extent in the final acetic acid. Although such carbonyl compounds may have little or no effect on the permanganate time, their removal is desired in order to improve the overall purity of the product.

The importance of purifying commercial acetic acid streams of various carbonyl contaminants (and especially reducing impurities) is apparent from the prior art references dealing with this problem. For example, U.S. Pat. No. 5,155,265 proposes reacting the carbonyl impurities with ozone to form a reactive oxygenated species or complex that can thereafter be more easily separated. This removal is carried out by passing the ozone-treated acetic acid through a carbonaceous material. Additionally, the effluent from this removal step is optionally contacted with a macroreticulated strong acid cation exchange resin which is stable in the acetic acid and has at least one percent of its active sites converted to the silver or mercury ion-exchange form.

U.S. Pat. No. 5,371,286, herein incorporated by reference, identifies particular intermediate streams in commercial acetic acid processing that contain relatively high concentrations of carbonyl impurities. Specifically, the overhead liquid stream from a commonly employed fractionator to separate primarily methyl iodide and acetic acid (referred to as the "splitter" column) tends to accumulate substantial quantities of carbonyl compounds, particularly acetaldehyde. If sufficient water is present, this stream will phase separate, with the carbonyl impurities partitioning preferentially into a heavy phase. In either case, the splitter column overhead or some portion thereof can be routed to another column for further processing by distillation and phase separation European patent 0487284 B1 proposes an alternate treatment of the splitter column overhead stream, which, as mentioned previously, has a significant content of carbonyl compounds compared to other intermediate process streams. Specifically, the splitter column overhead can be contacted with a solution of a compound that reacts with the carbonyls to facilitate subsequent separation by distillation. The reactive compound in this case is an amino compound such hydroxylamine in aqueous solution. The reaction of hydroxylamine and the carbonyl impurities in an oximation reactor produces oximes. The oximes in the reactor effluent are first phase separated in an aqueous phase and then distilled for removal of the oximation products.

In U.S. Pat. No. 5,625,095, the benefits associated with maintaining an acetaldehyde concentration in the reactor of 400 ppm or less are disclosed, particularly in terms of reducing the amounts of carbonyl impurities and organic iodides in the acetic acid product. Process conditions to reduce the acetaldehyde concentration are described, which may be used alone or in combination with specific extraction and distillation procedures. U.S. Pat. No. 5,783,731 discloses the treatment of the vent gas stream of the splitter column overhead stream to remove relatively high levels of acetaldehyde contained therein. The treatment involves condensing the vent gas stream and further contacting it with an aqueous amino compound to allow the separation procedure as outlined in the aforementioned European patent 0487284 B 1.

In addition to the manufacture of acetic acid, the incorporation of carbonyl impurities is problematic in commercial phenol production as well. Practically all phenol is currently manufactured via the oxidation of cumene to cumene hydroperoxide, followed by the decomposition of cumene hydroperoxide to phenol and acetone. Modem production requires the attainment of very high quality specifications to render the product phenol suitable as a precursor for bisphenol A, expoxy resins, and other downstream products. While previous specifications allowed as much as 100 ppm of carbonyl compounds, these limits are progressively being reduced to 10 ppm or less. The adsorption of carbonyl impurities as a means of achieving these low tolerances provides a favorable alternative to current separations involving distillation.

Overall, the prior art recognizes that adsorptive separation using resins may be applied to the removal of carbonyl impurities from aqueous and hydrocarbon streams. With respect to oxygenated organic liquids such as carboxylic acids and phenols, however, the prior art has unfortunately not offered such a simple and effective means of removing carbonyl impurities. While the prior art distillation methods outlined above can provide a reduction in the amount of detrimental carbonyl impurities, they unfortunately require significant resources in terms of energy, equipment, and manpower. The solutions offered thus far for the removal of carbonyl impurities from acetic acid, for example, involve complex and expensive schemes requiring fractionation.

In contrast, the adsorptive method of the present invention, which utilizes a resin having an amine functional group, is a simple solution to the recognized problem of carbonyl contamination in oxygenated organic liquids. The utility of a resin having capacity selective for the adsorption of specific types of carbonyl impurities (e.g. acetaldehyde) from a liquid that itself contains predominantly carbonyl compounds (e.g. acetic acid) or other oxygenates (e.g. phenol) is indeed unexpected. Furthermore, a simple regeneration procedure can restore the resin activity after at least a portion of its functional groups have been used for carbonyl impurity removal.

SUMMARY OF THE INVENTION

In one embodiment the present invention is a process for treating an oxygenated organic liquid containing a carbonyl impurity, the process comprising contacting the liquid with an adsorbent comprising a resin having an amine functional group at adsorption conditions and adsorbing the carbonyl impurity on the adsorbent to yield a treated liquid stream.

In another embodiment, the invention is a process as described above where the adsorbent has substantially reached its adsorption capacity, at which point the adsorbent is regenerated by contacting it with a basic liquid at regeneration conditions.

In a further embodiment, the invention is a process for producing purified acetic acid, the process comprising reacting methanol and carbon monoxide in a carbonylation zone to produce a carbonylated product; flash vaporizing the carbonylated product into a heavy-boiling recycle stream and a crude acetic acid product; recycling the heavy-boiling recycle stream to the carbonylation zone; separating the crude acetic acid product into intermediate acetic acid streams and a final acetic acid product; and contacting at least one of the final acetic acid product and the intermediate acetic acid streams with an adsorbent comprising a resin having an amine functional group to yield a treated liquid stream.

It is also within the scope of the invention to combine the above process with suitable pre- and post-treatment steps known in the art to further purify either the final acetic acid product, intermediate acetic acid streams, or the treated liquid stream. The process may also be integrated with downstream operations such as the production of vinyl acetate monomer (VAM) from acetic acid or the manufacture of purified terephthalic acid (PTA) using an acetic acid solvent.

DETAILED DESCRIPTION OF THE INVENTION

The feed stream for the process of the present invention includes broadly any oxygenated organic liquid containing a carbonyl impurity. Of commercial significance and particular applicability to the present invention are streams comprising predominantly carboxylic acids (e.g. acetic acid), phenols (e.g. phenol or bisphenol A), alcohols (e.g. methanol), anhydrides (e.g. acetic anhydride), and esters (e.g. methyl acetate). Typically, such streams are produced in industrial processes where the final product quality is of considerable importance, due to the impact of even trace impurities on the product stability and suitability for use in further processing operations. Of utmost concern to the present invention are oxygenated organic liquids resulting from either 1) the catalytic carbonylation of alcohols to produce carboxylic acids (e.g. acetic acid) or 2) the oxidation of aromatics to produce phenols (e.g. phenol).

In the particular case of modern methanol carbonylation technology to produce acetic acid, various commercial processes have been'developed and are described in detail in U.S. Pat. No. 3,769,329, U.S. Pat. No. 5,001,259, and other references. In general, the production process involves reacting methanol and carbon monoxide in a carbonylation zone (i.e. reactor), which is typically performed in the presence of catalyst having a metal function (e.g. rhodium or iridium) that is active for carbonylation. The resulting carbonylated reaction product is normally a mixture comprising acetic acid, methyl acetate, water, and methyl iodide. If a homogeneous (i.e. liquid phase) catalyst is employed, a substantial amount thereof will also be present in the carbonylation product.

The carbonylation product is flash vaporized to effect a separation of a crude acetic acid product in the vapor phase and a heavy-boiling recycle stream, often containing carbonylation catalyst, which is recycled back to the carbonylation zone. The crude acetic acid is then further separated by means comprising distillation, phase separation, extraction, and potentially other operations to provide a number of intermediate product streams and a final acetic acid product. Intermediate product streams, such as the aforementioned splitter column overhead stream, vary in type and composition depending on the specific methanol carbonylation process. In general, those streams having the highest concentrations of undesired carbonyl impurities are most suitable for the treatment process of the present invention. Otherwise, it is often most economical, for reasons explained below, to simply treat the final acetic acid product.

Regarding the final acetic acid product, varying levels of impurities are also present in this stream, depending on the specific methanol carbonylation process employed. Differences among the various industrial acetic acid production processes relate to reaction mixture compositions, separation schemes, and others that ultimately affect the final product composition. The acetic acid produced will normally contain a broad range of carbonyl impurities, that, as outlined in U.S. Pat. No. 5,783,731, include compounds containing saturated or unsaturated aldehyde or ketone functional groups. Specific types of carbonyl impurities known to contaminate commercially produced acetic acid, especially that made according to the low water processes described in U.S. Pat. No. 5,001,259 and U.S. Pat. No. 5,344,755, include, but are not limited to, acetaldehyde, butyraldehyde, crotonaldehyde, 2-ethyl crotonaldehyde, and 2-ethyl butyraldehyde. Because of their reducing ability, these carbonyl impurities, even if present in trace quantities in the acetic acid product, have an adverse affect on the product permanganate time test result, an important commercial measure of product quality. Acetic acid that is deficient with respect to permanganate time can present problems in downstream processing operations or may exhibit instability over periods of long-term storage.

To address commercial phenol manufacturing processes, many varieties of carbonyl impurities may appear in the final phenol product. The co-product acetone, for example, is a low-boiling carbonyl compound that is easily removed by distillation. Other carbonyls, however, are difficult or practically impossible to fractionate from the phenol product. These include, but are not limited to, hydroxyacetone, mesityl oxide, isophorone, and methyl benzofurans. Of these, hydroxyacetone is perhaps the most difficult to separate using conventional means. Currently, various methods exist for the removal of carbonyl impurities for the purification of phenol, but all of these techniques are highly energy intensive. A common procedure, for example, requires a crude phenol stream (after separation of acetone, cumene, alpha-methylstyrene, and high-boiling components) to be combined with steam and contacted in a phenol treating reactor with a mildly acidic catalyst such as silica-alumina or a zeolite. Under proper conditions, it is known that mesityl oxide can be hydrolyzed to acetone and that hydroxyacetone and phenol can be condensed to 2-methyl benzofuran. The reactor effluent is passed to a large fractionation tower where water is typically used as an extractive distillation agent. Purified phenol and high boiling components are recovered as a bottoms product while water and phenol at essentially azeotropic conditions are separated overhead. Due to the extractive distillation effect of water, 2-methyl benzofuran is also recovered with the low-boiling fraction and can be phase separated as an oily layer from the overhead receiver liquid. The bottoms phenol product from the extractive distillation is then routed to a rerun column where the final phenol product stream is removed as a low-boiling fraction. The high-boiling fraction, or bottoms of this rerun column, is typically recycled to the so-called "tar" or heavies column, which normally precedes the separation scheme described herein. The extractive distillation method, while effective for purifying phenol to 100 ppm by weight or less of carbonyl impurities, requires a large fractionator and substantial energy to boil the added extracting agent (e.g. water).

Other methods proposed for the removal of carbonyl impurities include the use of amine complexing agents such as hexamethylene diamine. Problems associated with this approach include the appearance of high-boiling amine-carbonyl complexes in the rerun column bottoms. If this stream is recycled to the aforementioned "tar" column, high reboiler temperatures will decompose these complexes, resulting in the release of carbonyl compounds back into the phenol product. If not recycled, the rerun column bottoms stream will represent a loss of not only the extracting agent, but also a significant proportion of the phenol product.

In contrast, the adsorptive method of the present invention provides a means to directly remove carbonyl impurities from a crude phenol product stream that would otherwise be directed to the phenol treating reaction and extractive distillation operations described above. In essence, the adsorptive separation eliminates these steps, along with the associated equipment and energy expenses, from the standard phenol purification flow scheme. Therefore, only conventional stripping (without extraction) and rerun fractionation towers are required for low- and high-boiling component removal, since the intermediate-boiling carbonyl impurities are now effectively adsorbed. Overall, the amine-substituted adsorbent effective for carbonyl impurity removal can be incorporated in place of the phenol treating reactor to treat the crude phenol stream. The extractive distillation column normally used is then converted to a simple stripping operation in this scenario. While this simplified flow scheme is suitable for new phenol production processes, existing commercial units might not be easily modified. For this reason, a practical alternative would be using the adsorbent of the present invention to treat the product (i.e. purified) phenol stream exiting in the rerun column overhead. Since this stream normally contains on the order of 100 ppm by weight of carbonyl impurities, the present invention can provide a means to realize more stringent targets in terms of carbonyl contamination of the final product. In a preferred embodiment, the adsorption process will reduce the level of carbonyl impurities in the treated liquid exiting the adsorbent bed to less than about 10 ppm.

In considering other types of oxygenated organic liquids that may be treated using the process of the present invention, final product streams of, for example, acetic acid or acetic anhydride production processes, where the product contains carbonyl impurities, are certainly applicable. Otherwise, it may be more economical to treat any of a multitude of intermediate process streams having an increased concentration of detrimental carbonyl compounds, compared to the final product. It should also be recognized that intermediate process streams may be treated to remove specific carbonyl compounds that are not themselves found to any significant degree in the final product, but are precursors to carbonyl impurities ultimately present in this product. For example, acetaldehyde is a precursor to higher molecular weight carbonyl impurities such as crotonaldehyde or higher aldol condensation products in the methanol carbonylation process environment.

In general, the term "intermediate acetic acid stream" includes all the process streams generated in reaction, distillation, phase separation, and other operations associated with the overall carbonylation of methanol to produce purified acetic acid. As mentioned, two industrially significant variations of these processes are disclosed in U.S. Pat. No. 3,769,329 and U.S. Pat. No. 5001259. Intermediate acetic acid streams in methanol carbonylation processes that are most applicable for the treatment process of the present invention are those having the highest concentrations of carbonyl impurities and thereby offering economically advantageous methods of treatment. Such streams are most often associated with the commonly used acetic acid-methyl iodide splitter column that effects a primary separation of the product. Specifically, as disclosed in the aforementioned U.S. Pat. No. 5371286 and U.S. Pat. No. 5,783,731, the splitter overhead receiver liquid and vent gas streams are known to contain relatively high concentrations (up to about 2 wt-%) of acetaldehyde. With respect to the overhead liquid, depending on the amount of water present, phase separation may lead to a further concentration of carbonyl impurities into a heavy, methyl iodide-rich stream particularly suitable for the adsorption process of the present invention.

Of course, treatment of the final product acetic acid stream is also an effective mode of carrying out the invention. Because the product stream is generally at or near the conditions of temperature and pressure most suitable for the adsorption of carbonyl impurities, there are normally no additional costs associated with heating, cooling, or pumping as might be incurred in the treatment of other process streams. A further consideration is that, depending on the various end uses of the acetic acid product, only a certain portion thereof may require treatment to remove carbonyl impurities. In this case, the product acetic acid stream, with all other factors being equal, is more likely to be the preferred feed stream to the adsorption process of the present invention.

The carbonyl impurity is in general any contaminant of the oxygenated organic liquid having the carbon-oxygen double bond characteristic of carbonyls. Depending on the specific oxygenated organic liquid, the carbonyl impurities may be ketones, aldehydes, oxides, furans, and the like. In the case of oxygenated liquids comprising a carbonylation product, preferred types of carbonyl impurities are reactive species that are detrimental to the overall quality of the oxygenated organic liquid, as measured using the aforementioned standard permanganate time test (STM. 170). Specifically, saturated and unsaturated aldehyde compounds meet this description. Ketone impurities such as acetone and methyl ethyl ketone, while not significantly affecting the product permanganate time, are also preferably adsorbed since they are often difficult to remove by conventional fractionation.

The carbonyl impurity, however, is not the same class of compound (e.g. carboxylic acid) as the oxygenated organic liquid. It is therefore not recommended to use the adsorption process of the present invention to separate, for example, propionic acid from acetic acid, as this separation is more amenable to distillation. In contrast, the present invention is most effective for the separation of different classes of carbonyls based on their respective differences in reactivity with the resin. Adsorption is especially advantageous over prior art distillation methods when the boiling point of the carbonyl impurity is near that of the oxygenated organic liquid. For example, the adsorption process of the present invention provides a simple and effective solution to the well-known problem of removing crotonaldehyde (b.p. 104° C.) from acetic acid (b.p. 118° C.).

The carbonyl impurity is present in the oxygenated organic liquid at a level of below about 50% by weight to be considered an impurity. Preferably, the carbonyl impurity concentration is from about 1 part per million (ppm) to about 20% by weight. Directionally, concentrations above this range more quickly expend the resin functional groups. Concentrations of carbonyl impurities below this range generally do not warrant the use of the adsorption method of the present invention. After treatment according to the process of the present invention, the treated liquid stream has a reduced concentration of undesired carbonyl impurities. The effectiveness of the treatment varies, of course, depending on the types of oxygenated organic liquids fed to the process and carbonyl impurities targeted for removal. In a preferred mode of operation corresponding to the treatment of carbonylation product streams (e.g. acetic acid), the treated liquid stream is depleted in carbonyl impurities to the extent that the permanganate time test of this material is at least about 120 minutes. For acetic acid, a permanganate time test result of 120 minutes is normally acceptable to commercial buyers.

As stated, resin-based adsorbents effective for the process of the present invention are generally those having an amine functional group. Without limiting the scope of the invention, it has been theorized that these amine functional groups are capable of reacting or complexing with carbonyl impurities to form an intermediate oximation reaction product or so-called Schiff base that remains affixed to the solid resin structure. For example, AG 4-X4 (available from Bio-Rad Laboratories, Richmond, Calif., a commercial weak anion resin having tertiary amine functional groups on an acrylic matrix, has been found to react with acetaldehyde impurities in an acetic acid stream. The reaction product, ethylideneazanol (an oxime), remains bound to the resin, thus effectively removing the carbonyl impurity according to the present invention. Compared to carrying out the oximation reaction in the liquid phase as outlined in European patent EP 0487284 B1 and U.S. Pat. No. 5783731, adsorption of carbonyl impurities onto a solid phase provides a significantly more convenient alternative. For instance, to costs associated with 1) continual injection of liquid reactant into the process, 2) the use of a homogeneous oximation reactor, and 3) subsequent separation of oximation products by distillation and extraction are all avoided.

In addition to the above mentioned AG 4-X4 resin, essentially any resin having amine functional groups can be used in the process of the present invention. In terms of performance, resins having tertiary amine functional groups are preferred over those having quaternary amine groups. Examples of preferred resins having at least some tertiary amine groups include, but are not limited to, AG 4-X4 and AG 3-X4 from Bio-Rad Laboratories (Richmond, Calif.) and Dowex WGR and Dowex MWA-1 from the Dow Chemical Company (Midland, Mich.).

The adsorption conditions used in the process of the present invention include an absolute pressure at least sufficient to maintain the feed stream as a liquid. In most cases, this absolute operating pressure is from about 0.1 to about 5 atmospheres (about 51 to about 1010 kPa). For convenience, atmospheric pressure is normally chosen. The adsorption temperature is preferably in the range from about 20° C. to about 100° C. In general, higher temperatures improve the interaction of the carbonyl impurities with the reactive amine functional groups of the resin. However, resin thermal degradation is a concern at temperatures above about 120° C. When the preferred continuous flow mode of operation is employed in the adsorption process, a suitable liquid hourly space velocity (LHSV) is in the range from about 0.1 to about 30 $hr^{-1}$. As understood in the art, the LHSV is the hourly volumetric liquid flow rate divided by the resin adsorbent volume and represents the reciprocal of the average time of the liquid within the adsorbent bed.

After an extended period of operation in carbonyl impurity removal service the reactive amine functional groups of the resin are expended through reaction. As substantially all of the amine groups are converted to resin-bound oximes, the resin gradually loses its effectiveness, so that the treated liquid stream may no longer conform to the product quality specifications demanded in terms of its permanganate time or other requirements. At this point, the resin has substantially reached its adsorption capacity and a simple regeneration procedure can restore its activity. Of course, resin regeneration may also be used even when the resin has only partially reached its adsorption capacity, but the economics of the operation in this case are generally less desirable.

Regeneration requires subjecting the resin, either in situ or ex situ, to a basic solution capable of restoring the resin amine functional groups while washing the adsorbed species from the resin as carbonyl compounds. Because the resin functional groups are re-established, the resin will again exhibit activity for carbonyl impurity removal. The regeneration procedure can be repeated multiple times to vastly extend the resin life. Regarding the mechanics of changing between the adsorption and regeneration phases of the present invention, it is possible to use swing-bed systems of the prior art to alternate beds of adsorbent between the adsorption and regeneration modes of operation. This will ensure a continual availability of active resin for the adsorption of carbonyl impurities.

The basic solution used for regenerating the resin after having partially or substantially reached its adsorption capacity can comprise an aqueous or an organic solution. Aqueous solutions are normally the most economical, with solutions of bases selected from the group consisting of sodium hydroxide, potassium hydroxide, ammonium hydroxide, sodium carbonate, and sodium bicarbonate being preferred. Sodium hydroxide is especially preferred. For purposes of regenerating the resin, concentrations of aqueous basic solutions in the range from about 0.01 to about 5 molar (or moles of base per liter of solution) are preferred. Below this range, an unnecessarily large amount of solution is required to regenerate the adsorbent. Above this range, the base concentration may be sufficiently strong to have a detrimental effect on the resin structure. For example, after the resin has undergone a period of service in the adsorption process of the present invention, a strong caustic solution can potentially attack the resin, destroying its functional groups, rather than restoring the amine function.

Other solutions that are effective for regenerating the resin include organic bases. Preferred types generally fall into the category of so-called "hindered amine" bases having secondary or tertiary amine groups. Examples of such organic bases include, but are not limited to, trimethylamine, triethylamine, pyrrolidine, piperidine, morpholine, piperazine, dialkylamines (e.g. diethylamine and n- and i-propylamine), pyridine, and all isomers of picoline. The organic bases may be used in pure form or diluted with a diluent such as water in which the organic base is at least partially soluble.

The regeneration of resin that has partially or substantially reached its adsorption capacity involves removing it from adsorption service and subjecting it to any of the above-mentioned basic solutions. It is not advisable to contact the base directly with a resin that is solvated with or immersed in an acidic solution such as acetic acid, since the resulting acid-base reaction could cause excessive heat release and damage the resin bed. Rather, an intermediate wash fluid such as water or other solution with a pH in the range from about 4 to about 10 should be used to rinse acidic media from the resin prior to regeneration. Water is normally preferred for convenience. During the rinsing with intermediate wash fluid, it is recommended to monitor the effluent solution pH to establish that essentially all acid is removed prior to subjecting the resin to the basic regeneration solution. In most cases, allowing the resin to dry between the adsorption and regeneration phases should be avoided to prevent problems associated with shrinkage/swelling of the resin bed.

This contacting of the resin with a base can be performed according to any means known in the art such as continuous flow or batchwise contacting. Continuous flow contacting through a fixed bed of the resin that has either partially or substantially reached its adsorption capacity is preferred. In this case, the flow rate of liquid base would be in accordance with a liquid hourly space velocity from about 0.1 to about 30 $hr^{-1}$. Other conditions associated with the regeneration procedure include a temperature from about 20° C. to about 100° C. and a pressure from about 0.1 to about 5 atmospheres. Ambient conditions of pressure and temperature are normally chosen for convenience.

It is within the scope of the invention to use a number of pre- or post-treatment steps in combination with carbonyl impurity adsorption to provide a high purity treated liquid stream. For example, when the process is used for the treatment of carbonyl impurity contaminated acetic acid that is produced by methanol carbonylation, metal cations may also be present in the acid. These cations are known contaminants originating from reaction catalysts (e.g. $Rh^{+3}$) or co-catalysts (e.g. $Li^{+1}$) or corrosion of the plant metallurgy (e.g. $Co^{+2}$). The removal of undesired cations in this case is taught in U.S. Pat. No. 5344976, hereby incorporated by reference. As described in this patent, a number of strong acid cation exchange resins, including Amberlyst® 15 (available from Rohm and Haas Company, Philadelphia, Pa.) are suitable and normally used in their hydrogen form.

Also pertaining to the treatment of commercial acetic acid streams is the need to remove molecular iodine and hydrogen iodide that result from the use of iodine-containing catalyst promoters in the reaction environment. The removal of these components may therefore also be combined with the carbonyl impurity adsorptive removal process of the present invention. For the removal of iodine and hydrogen iodide, the prior art teaches the use of various anion exchange resins, such as Reillex® 425, a crosslinked poly-vinylpyridine (available from Reilly Industries, Indianapolis, Ind. USA), Deloxan® THP (available from Degussa AG, Frankfurt, Germany), or Amberlite® IRA-958 (available from Rohm and Haas Company, Philadelphia, Pa., USA). The prior art also discloses the use of carbonaceous material, including activated carbons, activated carbon fiber, wood charcoal, bone char, lignite, and others that may be impregnated with alkali metals known to increase the inorganic iodine compound chemisorption capacity.

Another consideration related to the purification of acetic acid derived from methanol carbonylation is the removal of alkyl iodides and other iodine-containing compounds. The prior art also teaches this type of purification, which may be combined with the process of the present invention. U.S. Pat. No. 4,615,806, for example, discloses the use of silver exchanged resins for this service, while U.S. Pat. No. 5,962,735 teaches the use of silver exchanged zeolites.

Regardless of the use of any pre- or post-treatment steps, a significant objective of the treatment process of the present invention is to provide a treated product stream having quality attributes in terms of its permanganate test time and overall purity that render it suitable for further processing. As mentioned, for acetic acid in particular, two major uses are as a precursor for vinyl acetate monomer (VAM) production and as a solvent in the manufacture of purified terephthalic acid (PTA). The VAM process is well known in the art and described, among other references, in U.S. Pat. No. 5,990,344. The PTA process is also well know and described in, for example, U.S. Pat. No. 5,200,557, where acetic acid is a specific type of aliphatic carboxylic acid useful as a solvent in the reaction environment. Thus, in the case where acetic acid is purified according to the present invention to remove carbonyl impurities, it is contemplated that the treated liquid steam may be used in either a VAM or a PTA production process.

The adsorption process of the present invention may be carried out in any number of modes of operation. For example, the adsorption step can be performed using a fixed-,moving-, or fluidized-bed system or a batch operation. It is preferred to employ a fixed-bed system with the oxygenated organic liquid feed stream containing a carbonyl impurity continually flowing through the adsorption zone of active resin. Of course, the adsorption may also comprise a plurality of resin beds with the desired conditions maintained between and within the separate beds. The mechanics of this type of operation are known in the art.

The following examples are provided to clarify the invention but are not intended to limit in any respect the generally broad scope of the invention as described herein.

COMPARATIVE EXAMPLE 1

A mixture of acetic acid and acetaldehyde was prepared and analyzed using gas chromatography (GC). When the component concentrations determined by the analysis were normalized for unknown impurities, the mixture was determined to contain 89.3% acetic acid and 10.7% acetaldehyde by weight. A 20 gram portion of this mixture was contacted with 5 grams of Diphonix resin (available from ElChrom Industries, Darien, Ill.) in a batch autoclave overnight at 80° C. The Diphonix resin contains diphosphonate functional groups and is thus not a preferred type of resin for use in the present invention. After equilibration between the resin and acetic acid solution, the liquid was separated and found to contain normalized concentrations of 91.4% acetic acid and 8.6% acetaldehyde by weight. Based on this result, the resin showed a low capacity for the selective removal of acetaldehyde, a carbonyl impurity, from acetic acid. The performance of this resin was substantially poorer than the preferred resins of the present invention having amine functional groups. The adsorption capacity of the resin at 80° C. was calculated to be about 80 milligrams of acetaldehyde per gram of resin.

EXAMPLE 1

A mixture of acetic acid and acetaldehyde was prepared and analyzed using GC. When the component concentrations determined by the analysis were normalized for unknown impurities, the mixture was determined to contain 89.3% acetic acid and 10.7% acetaldehyde by weight. A 20 gram portion of this mixture was contacted with 5 grams of AG 3-X4 resin (available from Bio-Rad Laboratories, Richmond, Calif.) in a batch autoclave overnight at 80° C. As mentioned previously, AG 3-X4 resin contains primarily tertiary amine functional groups and is thus a preferred type of resin for use in the present invention. After equilibration between the resin and acetic acid solution, the liquid was separated and found to contain normalized concentrations of 99.0% acetic acid and 1.0% acetaldehyde by weight. Based on this result, the resin showed a significant capacity for the selective removal of acetaldehyde, a carbonyl impurity, from acetic acid. The adsorption capacity of the resin at 80° C. was calculated to be about 350 mg of acetaldehyde per gram of resin, which is substantially higher than the result obtained in Comparative Example 1, where the adsorbent did not have an amine functional group.

EXAMPLE 2

The batch experiment described in Example 1 was repeated except that the equilibration temperature was reduced from 80° C. to 60° C. Also, a new feed mixture was prepared and found to have normalized concentrations of 89.8% and 10.2% by weight of acetic acid and acetaldehyde, respectively, After equilibration with the AG 3-X4 resin overnight at the reduced temperature, the liquid was found to contain 96.9% acetic acid and 3.1% acetaldehyde by weight. Thus, the resin was again effective for selective removal of the acetaldehyde impurity from acetic acid, although performance was somewhat reduced at the lower equilibration temperature. The adsorption capacity of the resin at 60° C. was calculated to be about 280 milligrams of acetaldehyde per milliliter of resin, which is also substantially higher than the result obtained in Comparative Example 1, where the adsorbent did not have an amine functional group.

EXAMPLE 3

Using a 9 ml sample of the AG 3-X4 resin used in the batch experiments described in Examples 1 and 2, a continuous flow breakthrough test was performed to further evaluate the capacity of this resin for adsorption of the carbonyl impurity acetaldehyde from an acetic acid solution. The liquid stream fed to the resin in this experiment was acetic acid containing 0.89% by weight of acetaldehyde impurity. The resin was packed into a 10 mm i.d. column, through which the liquid feed was passed continuously. The carbonyl impurity adsorption conditions included an LHSV of 5 $hr^{-1}$, ambient pressure, and a temperature of 70° C.

Several effluent samples of the treated acetic acid were analyzed for acetaldehyde concentration during the course of the experiment. For the first 55 ml of acetic acid effluent exiting the resin bed, no acetaldehyde was detected, down to the 1 ppm limit of the GC instrument. The experiment was ended after treating 150 ml of contaminated acetic acid, at which point the effluent contained about 330 ppm of acetaldehyde.

EXAMPLE 4

After having partially reached its adsorption capacity, the resin from Example 3 was flushed with deionized water to remove residual acetic acid. A 300 ml portion of 5% by weight sodium hydroxide was passed over the resin to carry out the regeneration. The bed was again flushed with deionized water prior to re-use in the adsorptive removal of acetaldehyde from acetic acid. After this simple regeneration procedure, the resin bed was once again subjected to flowing acetic acid contaminated with 0.89% by weight of acetaldehyde, using the same process conditions as described in Example 3. The initial resin bed effluent samples after regeneration showed complete removal of the acetaldehyde, down to the 1 ppm detection limit of the GC.

What is claimed is:

1. A process for treating an oxygenated organic liquid containing a carbonyl impurity, the process comprising contacting the liquid with an adsorbent comprising a resin having an amine functional group at adsorption conditions and adsorbing the carbonyl impurity on the adsorbent to yield a treated liquid stream.

2. The process of claim 1 where the oxygenated organic liquid comprises a compound selected from the group consisting of carboxylic acids, phenols, alcohols, anhydrides, esters, and mixtures thereof.

3. The process of claim 2 where the oxygenated organic liquid comprises an intermediate acetic acid stream or a product acetic acid stream.

4. The process of claim 3 where the carbonyl impurity is an aldehyde or a ketone.

5. The process of claim 3 where the treated liquid stream has a permanganate time of at least about 120 minutes.

6. The process of claim 2 where the oxygenated organic liquid comprises a crude phenol stream or a product phenol stream.

7. The process of claim 6 where the treated liquid stream contains less than about 10 ppm by weight of carbonyl impurities.

8. The process of claim 6 where the carbonyl impurity is mesityl oxide or hydroxyacetone.

9. The process of claim 1 where the carbonyl impurity is present in an amount from about 1 ppm to about 20% by weight of the oxygenated organic liquid.

10. The process of claim 1 where the adsorption conditions include a temperature from about 20° C. to about 100° C., a pressure from about 0.1 to about 5 atmospheres, and a liquid hourly space velocity from about 0.1 to about 30 $hr^{-1}$.

11. The process of claim 1 further characterized in that the process is carried out until the adsorbent has substantially reached its adsorption capacity, at which point the adsorbent is regenerated by contact with a basic liquid at regeneration conditions.

12. The process of claim 11 where the basic liquid is an aqueous solution of a base selected from the group consisting of sodium hydroxide, potassium hydroxide, ammonium hydroxide, sodium carbonate, sodium bicarbonate and mixtures thereof.

13. The process of claim 12 where the base is present in a concentration from about 0.01 to about 5 molar.

14. The process of claim 11 where the basic liquid is an organic base selected from the group consisting of trimethylamine, triethylamine, pyrrolidine, piperidine, morpholine, piperazine, dialkylamines, pyridine, and picoline.

15. The process of claim 11 where the regeneration conditions include a temperature from about 20° C. to about 100° C., a pressure from about 0.1 to about 5 atmospheres, and a liquid hourly space velocity from about 0.1 to about 30 $hr^{-1}$.

16. A process for producing purified acetic acid, the process comprising:
(a) reacting methanol and carbon monoxide in a carbonylation zone to produce a carbonylated product;
(b) flash vaporizing the carbonylated product into a heavy-boiling recycle stream and a crude acetic acid product;
(c) recycling the heavy-boiling recycle stream to the carbonylation zone;
(d) separating the crude acetic acid product into intermediate acetic acid streams and a final acetic acid product; and
(e) contacting at least one of the final acetic acid product and the intermediate acetic acid streams with an adsorbent comprising a resin having an amine functional group to yield a treated liquid stream.

17. The process of claim 16 where, prior to step (e), at least one of the final acetic acid product and the intermediate acetic acid streams is pretreated to remove an impurity comprising a metal or an iodine-containing compound.

18. The process of claim 16, where, after step (e), the treated liquid stream is post-treated to remove an impurity comprising a metal or an iodine-containing compound.

19. The process of claim 16 where the treated liquid stream has a permanganate time of at least about 120 minutes.

20. The process of claim 16 where the treated liquid steam is used in a vinyl acetate monomer or a purified terephthalic acid production process.

* * * * *